United States Patent
Lundgreen et al.

(10) Patent No.: US 9,052,302 B2
(45) Date of Patent: Jun. 9, 2015

(54) METHOD FOR DETERMINING AN ANALYTE IN A WATER SAMPLE BY MEANS OF A MOBILE WATER ANALYSIS ARRANGEMENT

(75) Inventors: Ulrich Lundgreen, Geutersloh (DE); Aria Farjam, Duesseldorf (DE); Rolf Uthemann, Leverkusen (DE); Andreas Mitreiter, Kleinmachnow (DE); Isabel Huenig, Duesseldorf (DE); Markus Lenhard, Viersen (DE); Rainer Froemel, Troisdorf (DE); Hans-Joachim Kumpch, Berlin (DE)

(73) Assignee: HACH LANGE GMBH, Berlin (DE)

( * ) Notice: Subject to any disclaimer, the term of this patent is extended or adjusted under 35 U.S.C. 154(b) by 499 days.

(21) Appl. No.: 13/122,561

(22) PCT Filed: Sep. 28, 2009

(86) PCT No.: PCT/EP2009/062535
§ 371 (c)(1),
(2), (4) Date: May 10, 2011

(87) PCT Pub. No.: WO2010/040657
PCT Pub. Date: Apr. 15, 2010

(65) Prior Publication Data
US 2011/0212538 A1    Sep. 1, 2011

(30) Foreign Application Priority Data
Oct. 6, 2008    (DE) .......................... 10 2008 050 092

(51) Int. Cl.
*G01N 33/18*    (2006.01)
*G01N 21/31*    (2006.01)
*B01L 3/00*    (2006.01)

(52) U.S. Cl.
CPC ........... *G01N 33/1893* (2013.01); *B01L 3/5027* (2013.01); *G01N 21/3151* (2013.01); *G01N 33/1886* (2013.01); *G01N 2201/0245* (2013.01)

(58) Field of Classification Search
None
See application file for complete search history.

(56) References Cited

U.S. PATENT DOCUMENTS 5,386,287 A    1/1995    Berssen et al.
5,572,328 A    11/1996    Fouckhardt et al.
(Continued)

FOREIGN PATENT DOCUMENTS

CN    1250160 A    4/2000
DE    41 09 118 A1    9/1992
(Continued)

OTHER PUBLICATIONS

Grover et al., "Monolithic membrane valves and diaphragm pumps for practical large-scale integration into glass microfluidic devoices", Sensors and Actuators B, 2003, v. 89, pp. 315-323.*
(Continued)

*Primary Examiner* — Sam P Siefke
(74) *Attorney, Agent, or Firm* — Norman B. Thot (57) ABSTRACT

A method for determining an analyte in a water sample with a mobile water analyzing system having a basic unit and a test element insertable in the basic unit, the method comprising providing the test element and the basic unit. The test element is inserted into a test element receptacle of the basic unit. The water sample is transported forward from an inlet opening to a measuring section of the test element. A first analyzing of the water sample is performed in the measuring section with an analyzer of the basic unit. The water sample is transported forward from the measuring section to the first reagent section of the test element. The water sample is transported backward from the first reagent section to the measuring section of the test element. A second analyzing of the water sample is performed in the measuring section with the analyzer of the basic unit.

17 Claims, 6 Drawing Sheets

(56) References Cited

U.S. PATENT DOCUMENTS

| | | |
|---|---|---|
| 5,731,212 A | 3/1998 | Gavin et al. |
| 5,821,405 A | 10/1998 | Dickey et al. |
| 5,844,686 A | 12/1998 | Treptow et al. |
| 5,993,742 A | 11/1999 | Binz et al. |
| 6,596,237 B1 | 7/2003 | Borrelli et al. |
| 7,459,713 B2 | 12/2008 | Coates |
| 7,491,366 B2 | 2/2009 | Tokhtuev et al. |
| 2004/0098211 A1 | 5/2004 | Binz et al. |
| 2004/0109790 A1 | 6/2004 | Shartle et al. |
| 2004/0154933 A1 | 8/2004 | Cosofret |
| 2005/0037508 A1 | 2/2005 | Hernandez et al. |
| 2007/0144277 A1 | 6/2007 | Padmanabhan et al. |
| 2008/0227185 A1 | 9/2008 | Schonfeld et al. |
| 2008/0241966 A1 | 10/2008 | Kunnecke et al. |
| 2008/0265146 A1 | 10/2008 | Coates |
| 2009/0009768 A1 | 1/2009 | Jiang et al. |
| 2010/0009336 A1 | 1/2010 | Sullivan |
| 2011/0212538 A1 | 9/2011 | Lundgreen et al. |
| 2011/0217213 A1 | 9/2011 | Chen et al. |
| 2012/0021527 A1 | 1/2012 | Salzer et al. |
| 2012/0305394 A1 | 12/2012 | Bae et al. |

FOREIGN PATENT DOCUMENTS

| | | |
|---|---|---|
| DE | 101 26 054 A1 | 6/2002 |
| EP | 0 821 231 A2 | 1/1998 |
| EP | 1 506 813 A1 | 2/2005 |
| EP | 1 764 153 A2 | 3/2007 |
| EP | 1 870 033 A1 | 12/2007 |
| EP | 2 266 691 A1 | 12/2010 |
| WO | WO 02/074043 A2 | 9/2002 |
| WO | WO 2008/137260 A1 | 11/2008 |
| WO | WO 2010/040657 A1 | 4/2010 |

OTHER PUBLICATIONS

"2320 Alkalinity" section of the American Public Health Association's publication Standard Methods (2005).

Hach Company APA 6000™ Alkalinity 2001 Operation Manual.

J. S. Fritz et al.: "Quantitative Analytical Chemistry", Fifth Edition, Boston, pp. 151-154 (1987).

\* cited by examiner

METHOD FOR DETERMINING AN ANALYTE IN A WATER SAMPLE BY MEANS OF A MOBILE WATER ANALYSIS ARRANGEMENT

CROSS REFERENCE TO PRIOR APPLICATIONS

This application is a U.S. National Phase application under 35 U.S.C. §371 of International Application No. PCT/EP2009/062535, filed on Sep. 28, 2009 and which claims benefit to German Patent Application No. 10 2008 050 092.5, filed on Oct. 6, 2008. The International Application was published in German on Apr. 15, 2010 as WO 2010/040657 A1 under PCT Article 21(2).

FIELD

The present invention provides a method for determining an analyte in a water-sample with a mobile water-analyzing system. The present invention also provides a mobile water-analyzing system for determining the aforementioned method as well as a basic unit and a test-element of the respective mobile water-analyzing system. "Mobile" means that the water-analyzing system of the present invention is not stationary as a continuously working process analyzing-device.

BACKGROUND

The prior art in the field of mobile water-analysis is currently represented by so-called photometric cuvette tests as described in DE 41 09 118 A1. The use of these tests is performed manually. First, a water-sample is taken by a pipette and given into the cuvette. For determining the self-absorption of the water-sample, i.e., the so-called background signal, the water-sample is inserted into the photometer and is measured. A reagent is then added to the water-sample in the cuvette. The cuvette is closed and shaked to mix the water-sample with the key-reagent. It is subsequently inserted into a photometer and measured.

The handling of such a cuvette test is inconvenient and extremely susceptible to errors. The used reagent can be dangerous for health and the environment, so that the used cuvette tests must be disposed in an appropriate way. The inconvenient handling makes the cuvette tests only applicable for use in a laboratory. Such water-sample analyzation, including the determination of the self-absorption of the water-sample, can be performed automatically in a non-mobile water-analyzing system.

SUMMARY

An aspect of the present invention is to provide a method or a device for determining an analyte in a water-sample including the determination of the self-absorption of the water-sample with a mobile water-analyzing system with improved handling.

In an embodiment, the present invention provides a method for determining an analyte in a water sample with a mobile water analyzing system having a basic unit and a test-element insertable in the basic unit which includes providing the test element comprising a sample line with an inlet opening configured to receive the water sample, a measuring section forming a measuring track and configured to allow determination of the analyte, a first reagent section disposed behind the measuring section, and a reagent disposed in the first reagent section of the sample line. The basic unit is provided comprising a test element receptacle configured to hold the inserted test element and an analyzer with an analyzer measuring track formed by the measuring section of the test element. The test element is inserted into the test element receptacle. The water sample is transported forward from the inlet opening to the measuring section. A first analyzing of the water sample is performed in the measuring section with the analyzer. The water sample is transported forward from the measuring section to the first reagent section. The water sample is transported backward from the first reagent section to the measuring section. A second analyzing of the water sample is performed in the measuring section with the analyzer.

BRIEF DESCRIPTION OF THE DRAWINGS

The present invention is described in greater detail below on the basis of embodiments and of the drawings in which.

DETAILED DESCRIPTION

The method for determining an analyte in a water-sample refers to a mobile water-analyzing system with a mobile basic unit and a removable disposable test-element which is inserted or is insertable, respectively, into the basic unit for determining the analyte.

The test-element is a complex prefabricated part, whereby the test-element is provided with a sample-line with an inlet opening which is positioned at the distal end of the test-element. A measuring section is provided in line of the sample-line, the sample-line being provided with a measuring track for an analyzer which is provided at the basic unit. All other parts of the analyzer are positioned in the basic unit and not in the test-element. The basic unit is further provided with a receptacle for holding the inserted test-element.

In the further course of the sample-line, a reagent section is provided, for example, a section after the measuring section as seen from the inlet opening. The reagent section is provided with a reagent which can be, for example, a key-reagent, an auxiliary-reagent or an auxiliary-agent. A key-reagent reacts with the analyte of the water-sample by changing the color of the analyte, or the key-reagent reacts in such a way that an electrochemical analysis is possible. An auxiliary-reagent also reacts with the water-sample, but not with the aim of a quantitative determination of the analyte in the water-sample, but rather with another aim. An auxiliary-agent does not react chemically with the water-sample but influences the water-sample.

According to the present invention, the inserting of the test-element into the test-element receptacle of the basic unit is first provided. The inserting of the test-element can be performed manually or automatically. The inlet opening of the test-element is then immersed manually or automatically into the water to be analyzed and a defined portion or a defined volume, respectively, of the water-sample is segregated by transporting the water-sample forward so that the water-sample is transported from the inlet opening to the measuring section.

The creation of a defined portion of the water-sample can be realized automatically or semi-automatically: The insertion of the test-element into the test-element receptacle of the basic unit activates the basic unit for an analyte determination. In a next step, the inlet opening of the test-element is immersed manually or automatically into the water-reservoir to be analyzed. After the immersion of the inlet opening into the water-reservoir, the pump actuator is activated, whereby the immersion can be detected, for instance, through a small pressure impulse in the sample-line. The activating of the pump actuator can also be performed manually. By activation of the pump actuator, a water-sample is pumped actively through the inlet opening toward the measuring section.

A defined volume of the water-sample is sucked and is segregated as a sample-column, whereby the sample column at both ends is limited by air. By limiting the sample-column to a defined volume, a defined ratio between the water-sample and the key-reagent is provided.

The limitation of the water-sample portion to a defined portion can be realized by giving the customer a signal after the pump actuator has stopped after a defined volume of the water-sample has been sucked so that the customer obtains the information that the sampling is finished and that the inlet opening can be taken out of the water to be analyzed. The first segregation of the water-sample can also be made automatically by using an appropriate valve which conducts air into the sample-line after the defined water-sample volume is sucked.

"Pumping forward" means a transporting in the sample-line upstream from the inlet opening. The forward pumping can be performed in any known way, for example, by a pump in the basic unit, whereby the pump is connected with the sample-line, or by a relative large pump volume which is formed by a pump-membrane at the disposable test-element, whereby the pump-membrane is controlled via a pump actuator of the basic unit, for example, by a push rod.

In the measuring section, a first analysis of the water-sample is performed with the analyzer, for example, a sample background signal is determined. The first analysis can also basically be a quantitative determination of an analyte in the water-sample when a key-reagent is positioned in the sample-line between the inlet opening and the measuring section.

The analyzer can be an electrochemical analyzer which determines an electrical parameter of the water-sample. Alternatively or additionally, the analyzer can be a photometer with a light source and a light detector.

As soon as the first analysis is finished, the water-sample is transported forward from the measuring section to the first reagent section. The water-sample is mixed in the first reagent section with the first reagent. The first reagent can be a key-reagent, for example, a reagent which colors the analyte of the water-sample. The first reagent can alternatively be an auxiliary-reagent or an auxiliary-agent of another nature, for example, if a key-reagent is positioned between the inlet opening and the measuring section.

The first reagent can, for example, be a key-reagent which, for example, reacts with the analyte of the water-sample, whereby the reaction changes the optical or the electrochemical properties of the water-sample. Referring to the example of a photometrical analyzer, the absorption spectra of the water-sample changes particularly at defined spectra lines or defined spectra areas, respectively. The first reagent can also be an auxiliary-reagent which is not a detection-reagent or another auxiliary-agent.

The prepared and homogenized water-sample, whereby the mixing of the water-sample is performed, for example, by repeatedly pumping back and forth, can be transported backward from the first reagent-section to the measuring section, whereby the water-sample can be analyzed a second time by the analyzer electrically and/or optically. The result of the second analysis can, for example, be a gross-value. For example, the background signal of the sample of the first analysis can be subtracted from the gross-value and lead to a net value of the analyte in the water-sample. The net-value can be displayed and/or saved. As soon as the net-value is displayed, the disposable test-element can be removed manually or automatically.

All steps which are relevant for the quality of the measurement results of the water analysis, such as the analysis, for example, determining the background signal of the sample, the dosage of the first reagent, for example, the mixing of the first reagent with the water-sample, the waiting for the reaction time etc., can be performed semi-automatically or fully-automatically, respectively, and air-tight. Errors and hazards resulting from inaccurate handling can therefore be almost totally excluded.

In an embodiment, the present invention provides a method for a disposable test-element, whereby the test-element is provided with a sample-line and a measuring section, whereby the water-sample is pumped forward after a first analysis of the water-sample in the measuring section to a first reagent-section in order to be mixed with the reagent and pumped backward to the measuring section to be analyzed again. The water-sample can be mixed with the key-reagent before the first analysis or can be transported free of reagent to the measuring section to perform a first analysis, for example, to determine a background signal of the sample. The positioning of a reagent in a first reagent section which is behind the measuring section allows numerous options to perform one or several analysis, respectively, and to improve further properties of the disposable test-element.

According to an embodiment of the method of the present invention, the sample-line can, for example, be provided with a second reagent section with a second reagent which can, for example, be an auxiliary-agent, whereby the second reagent section can be positioned beyond the first reagent section. The following method steps are performed subsequently to the water-sample analysis:

transporting the analyzed water-sample forward to the second reagent section.

The water-sample reacts in the second reagent-section with the second reagent, for example, with an auxiliary-agent. A second reagent behind and separated from the first reagent or first reagent-section, respectively, as seen from the measuring section, allows the realization of numerous additional functions. For example, the second reagent can be an auxiliary-agent which is formed as a gelling agent and/or color agent so that the water-sample is gelatinized and/or colored after the analysis of the water-sample. Gelatinizing causes a fixation of the water-sample in the sample-line so that leakage is avoided. Changing the color of the water-sample shows the customer and/or the analyzer which detects the change of the optical properties that the disposable test-element is already used.

The water-sample can, for example, be transported backwards from the second reagent section to measuring section, so that the water-sample can be analyzed a third time by the analyzer. A third reagent section can be positioned behind the second reagent section, for example, with a second auxiliary-agent, whereby the following method steps are performed subsequently to the third analyzing of the water-sample:

transporting the water-sample forward to the third reagent section;

transporting the water-sample backward from the third reagent section to the measuring section; and performing a fourth analyzing of the water-sample with the analyzer.

Both auxiliary-agents in both auxiliary-agent sections, for example, the second and the third reagent section, can, for example, be analyte-standards with different respective quantities or concentrations. The described method allows the performance of a standard-addition so that a calibration can be performed at each measuring sequence. The actual and exact concentration of the analyte in the water-sample can be determined by calculating the regression of the result of the key-reagent analysis of the water-sample.

It is also possible to provide more than two reagent sections with respective auxiliary-agents or analyte-standards, respectively, so as to increase the accuracy of the calibration, for example, with non-linear characteristics.

The test-element can physically have a size of a flat match stick so that the sample-line can have a corresponding small cross-section, which is in a range between 0.01 $mm^2$ and some square millimeters. The photometrical section or the measuring track, respectively, should be as long as possible, for example, in the range of some millimeters to some centimeters. The volume of the water-sample in the photometrical section is therefore in the range of one to about one hundred cubic millimeters. According to the dimensions, the amount of the reagent is small so that the potential danger for health and the environment is low as well. The need for an appropriate disposure can therefore be avoided so that a considerable effort for the appropriate disposure or recycling to the distributor or producer, respectively, can be avoided.

All steps which are relevant for the quality of the measurement results of the water analysis, such as the dosage of the analyte, the mixing of the analyte with the water-sample and the waiting for the reaction time etc., are performed semi-automatically or fully-automatically, respectively, and air-tight. Errors and hazards resulting from inaccurate handling can therefore be almost completely excluded.

The analyzer can, for example, be a photometer with a light source for generating a measurement beam and a light detector for receiving the measurement beam, whereby the measuring section which is passed through by the beam can be formed by a photometer section. The photometer can, for example, be provided as a transmission-photometer. A transmission-photometer has, compared with a reflection-photometer, a better information signal. The transmission-photometer allows for a more precise quantitative determination of an analyte at a relative short measuring track. The measuring section can be provided with at least one photometrical-window for the inlet and the outlet of the measurement beam. With the photometrical method, different ions, for example, chlorine, phosphate and ammonium, can be measured.

The analyzer can alternatively be an electrochemical analyzer which determines an electrical parameter in the measuring section. The measuring section can be provided with at least one electrode or sensor area, respectively, which is connected through electric lines with contacts or contact areas of the test-element, respectively. The contacts of the test-element can be connected with the basic unit through contacts or through contact areas, respectively, and therefore with the analyzer of the basic unit. The electrode or sensor area, respectively, has an area of some square micrometers to some millimeters. Different parameters, for example, conductivity, redox potential, pH-value and oxygen content oxygen, can be measured with the electrochemical method.

The basic unit can alternatively be provided with a photometrical, an optical or an electrochemical analyzer, respectively, so that photometrical, optical and also electrochemical test-elements can alternatively be used at the basic unit.

The test-element can be provided with a positioning element which can provide an exact positioning of the test-element in the basic unit. The measuring section of the test-element must be exactly in line with the photometer of the basic unit to provide a photometrical measurement without errors. The test-element can therefore be provided with at least one separate positioning element, which provides the positioning in addition to the lateral surface of the test-element in the basic unit. For example, the test-element can comprise a groove, a cavity or an opening in which a respective snap element of the basic unit snaps in so as to position and fix the test-element into the basic unit.

The reagent or the reagents, respectively, can, for example, be provided in a dry state in the sample-line. It is also possible to arrange numerous different key-reagents or detection-reagents in series in the sample-line behind the measuring section. Once the water-sample arrives at the respective key-reagent, the reagent is dissolved in the water-sample and reacts with the analyte, for example, by changing the color.

The test-element can, for example, be provided with a pump-membrane which can be controlled via a pump actuator of the basic unit, whereby the pump actuator can be provided, for example, with an electromotive rod. The flexible pump-membrane can be positioned at the opposite end as seen from the inlet opening on the sample-line and seals the pump opening of the sample-line air-tight so that air is pushed and the water-sample is transported in the sample-line by a deformation of the pump-membrane. Pushing or deformation, respectively, of the pump-membrane causes a transporting of the fluid backward, while releasing of the pump-membrane causes a transporting of the fluid forward in the sample-line. The releasing of the membrane can be performed by the resilience of the membrane or by pulling the membrane with the pump actuator. Both the pump-membrane and the pump actuator can form a membrane-pump, whereby the test-element can be provided with the pump-membrane. The electromotive pump actuator or the rod, respectively, can be positioned in the basic unit.

The test-element can alternatively be provided with a pump-opening in the sample-line. The pump-opening can be positioned at the opposite end as seen from the inlet opening on the sample-line. The basic unit can be provided with sample pump which is connected with the inserted test-element as soon as the test-element is inserted in the basic unit.

In an embodiment of the present invention, an absorption body can, for example, be arranged between the measuring section and the pump opening. The absorption body serves to absorb the water-sample after the water-sample has been finally analyzed and is transported forward to the absorption body. The water-sample can thereby be immobilized and a leakage of the water-sample avoided. For example, the absorption body can be a fleece body, a clay body like bentonite or can be a so called super-absorber. The body can additionally comprise a neutralizing reagent.

In an embodiment of the present invention, the sample-line can, for example, be provided with a sample filter which filters the water-sample which is sucked through the inlet opening of the test-element. The filtration can be performed before the water-sample is transported to the measuring section to be analyzed, for example, analyzed photometrically. The sample filter can be made of mineral wool.

According to an embodiment of the present invention, the sample-line can, for example, be provided with a dose capillary which can be arranged between the inlet opening and the measuring section. The dose capillary can, for example, be arranged adjacent to the inlet opening. By using a dose capillary, the water-sample can be sucked, basically by the capillary force, into the test element so that a defined water-sample volume can be segregated. The water-sample can thereafter be pumped repeatedly forth and back inside the sample-channel by using the pump actuator.

The test-element can be provided with a drying agent to protect the key-reagent against humidity. For example, the drying agent can be separated in the sample-line by using a hydrophobic stopper capillary, whereby the humidity can flow through the stopper capillary to the drying agent.

The inlet opening and/or the pump opening can be sealed with a humidity-tight transport-seal which can be opened manually or automatically by inserting the test-element into the basic unit, for example, by piercing. The single test-element can alternatively or additionally be sealed in a humidity-tight package.

Figure 1:
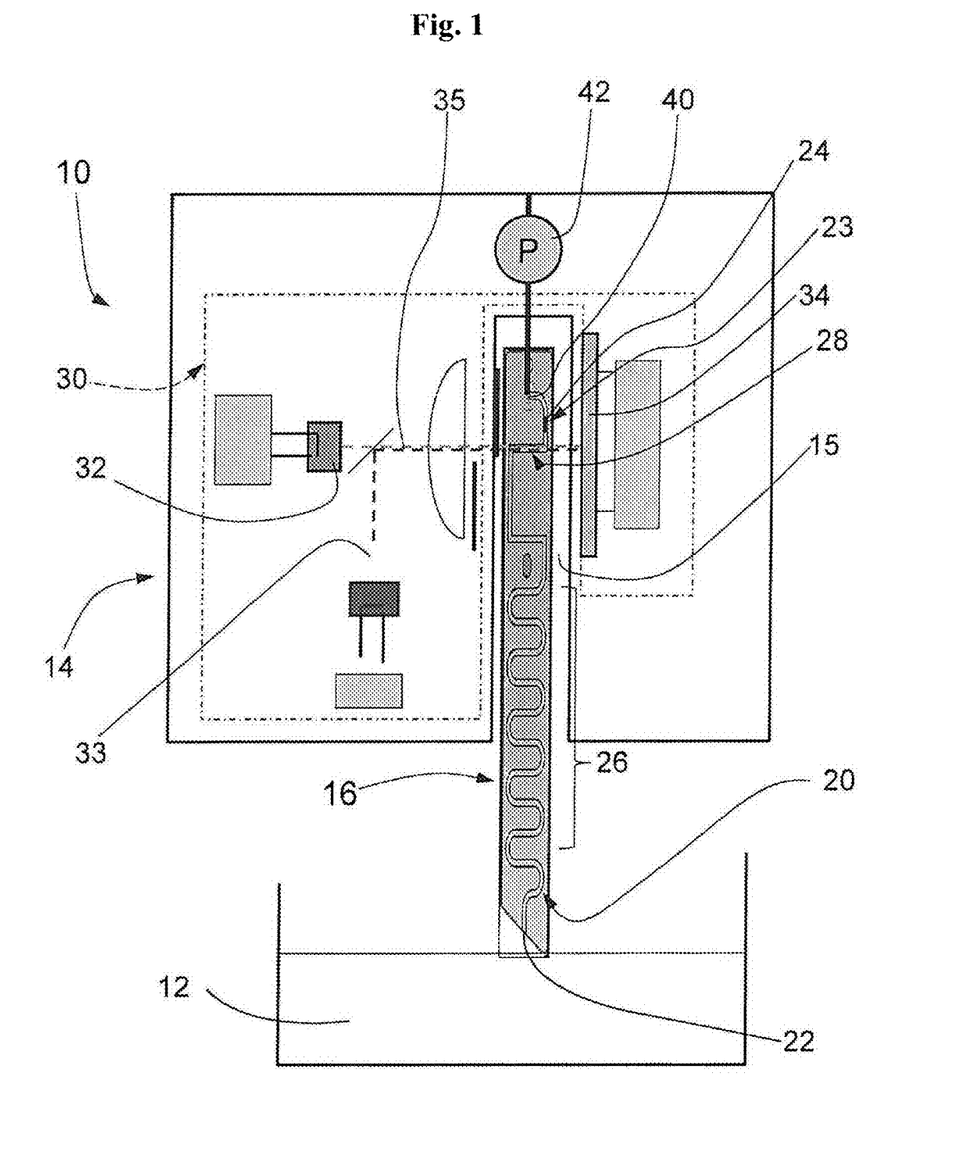
FIG. 1 shows a schematic drawing of a mobile water-analyzing system comprising a basic unit and a test-element, to determine the method according to the present invention.
Figure 3:
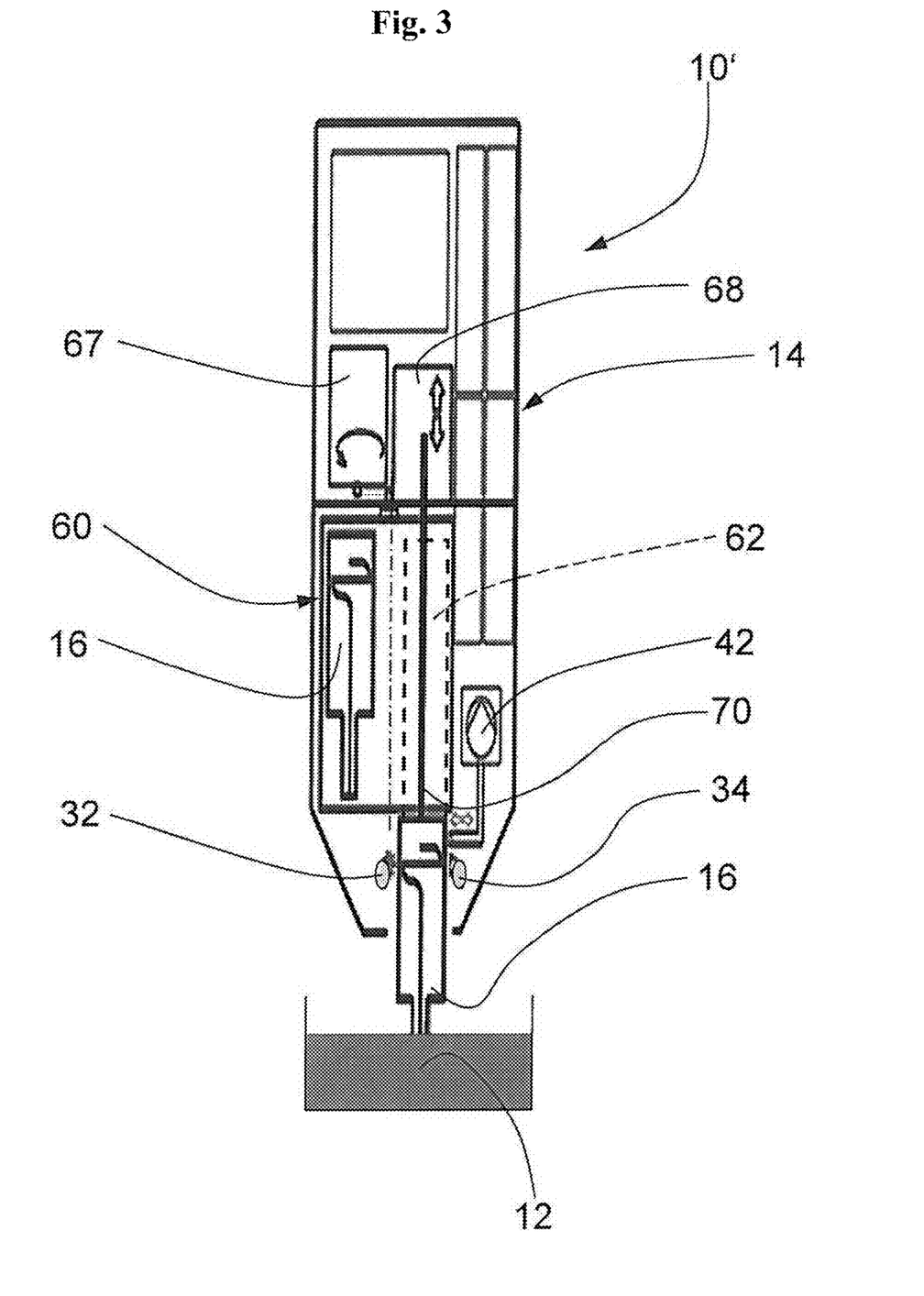
FIG. 3 shows an embodiment of a mobile water-analyzing system including a removable cartridge with several test-elements, to determine the method according to the present invention.

FIGS. 1 and 3 schematically show a mobile water-analyzing system 10, 10' for a quantitative determination of an analyte in a water-sample. With the described embodiment of a photometrical analyzing system 10, 10', chlorine, phosphate or ammonium can be determined. Alternatively or additionally, the analyzing system can be provided as an electrochemical analyzing system with an electrical analyzer.

The analyzing system of FIG. 1 comprises a basic unit 14 and a removable disposable test-element 16 which is presently inserted into the basic unit 14.

Figure 2:
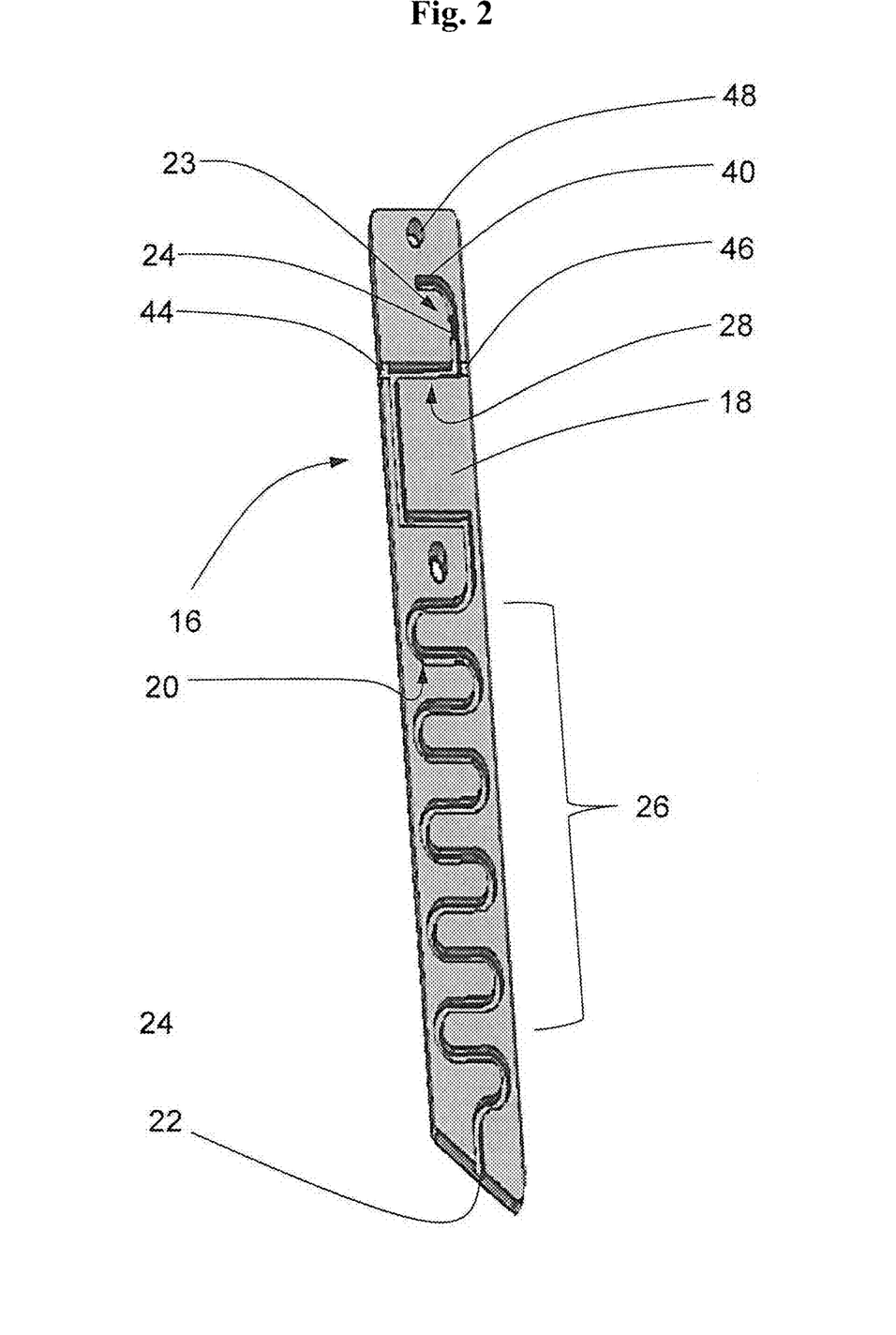
FIG. 2 shows the test-element of the water-analyzing system of FIG. 1.

The test-element 16 is provided with a test-element body 18 made of plastic. The test-element body 18 is provided with a sample-line 20 which is formed as a groove. The side of the groove opening of the test-element body 18 is closed with a transparent plastic film or aluminum cover, respectively (not shown).

The sample-line 20 is provided with an inlet opening 22 which is positioned at the distal end, referring to the basic unit 14, and through which a water-sample is sucked from a water-reservoir 12. Adjacent to and, in the flow direction, behind the inlet opening 22. is a meander-like mix section 26 of the sample-line 20 in which a key-reagent, an auxiliary-reagent or an auxiliary-agent and the sucked water-sample are homogeneously mixed.

A measuring section 28 is arranged adjacent to the mix section 26 in which a quantitative determination can be performed. The present measuring section 28 is a photometrical section, whereby the measuring section 28 forms a measuring track for the respective photometrical analyzer 30 of the basic unit 14. Both sides of the photometer section 28 comprise a clear-transparent photometrical window 44, 46 as shown in FIG. 2. The test-element body 18 can be completely made out of a clear transparent plastic which allows the measuring beam 35 to pass through the measuring section 28.

Proximal to the measuring section 28, i.e., behind the measuring section 28 as seen from the inlet opening 22, is a reagent section 23 with a dry reagent 24 which is a key-reagent. At the sample-line end opposite to the inlet opening 22, i.e., behind the first reagent section 23, a pump opening 40 as a pump element is provided which is connected with a pump actuator of the sample pump of the basic unit when the test-element is inserted into the basic unit 14.

The basic unit 14 is provided with an analyzer 30 which is a transmission photometer with two light sources 32, 33 and a light detector 34. The light-sources 32, 33 emit light of different wavelengths and the light detector detects both wavelengths.

The test-element 16 is provided with a positioning element 48 which is realized as an opening. The positioning element 48 cooperates with a respective snap element of the basic unit 16 so that the test-element 16 is fixed reproducibly and exactly. This provides that the measuring beam 35 generated by the light source 32, 33 is exactly in line with the photometrical measuring section 28. The test-element receptacle of the basic unit 14 is formed as a slot 15 in which the test-element 16 fits without any clearance.

Figure 4:
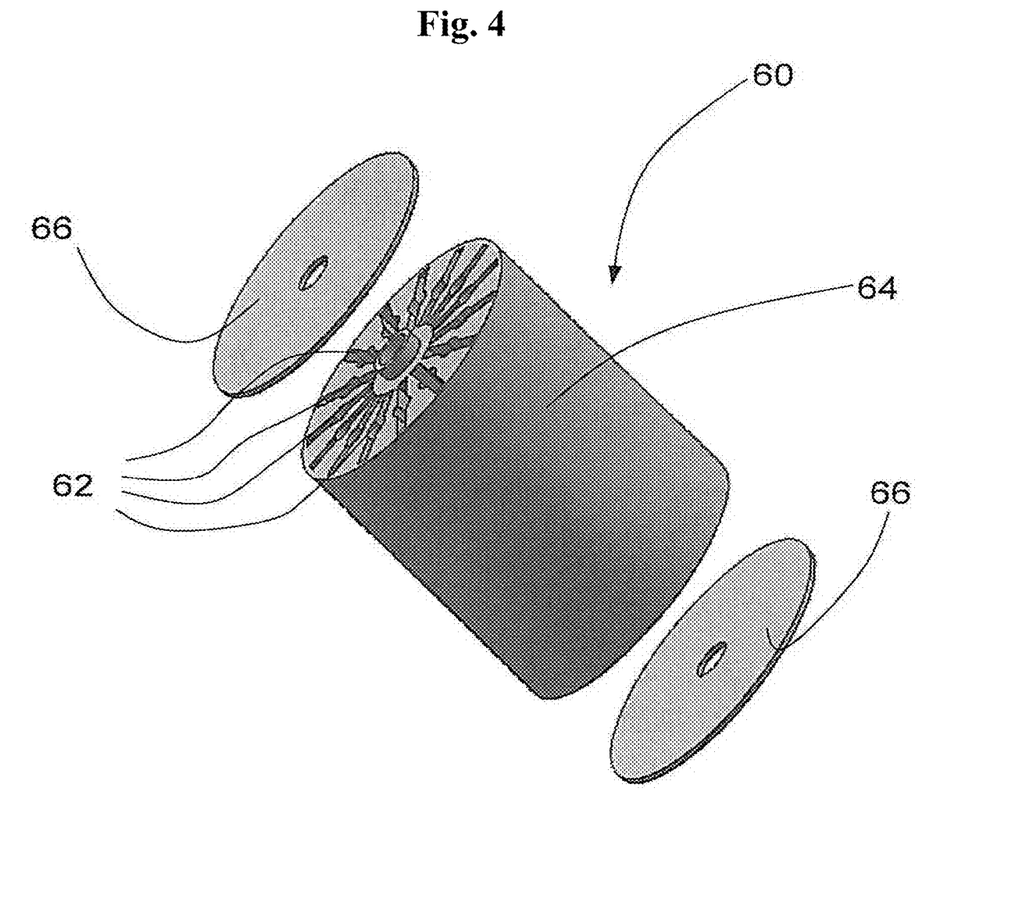
FIG. 4 shows the removable cartridge of FIG. 3.

FIG. 3 shows a second embodiment of a mobile water-analyzing system 10' including a removable cartridge 60 which is formed as a drum with 15 drum chambers 62, whereby each drum chamber 62 carries a test-element 16. The plastic drum body 64 is sealed axially with a circular sealing foil 66 so that the chambers 62 are sealed gas-tight and fluid-tight.

As shown in FIG. 3, the removable cartridge 60 is inserted into a respective cartridge slot of the basic unit 14'. The basic unit 14' is provided with a cartridge rotary actuator 67 and a test-element shifter 70. The shifter 70 can shift a test-element 16 automatically from a chamber 62 into the measuring position as shown in FIG. 3.

As soon as the measurement is finished, the shifter 70 moves the test-element 16 out of the measuring position and ejects it out of the basic unit 14'. In a next step, the shifter 70 is completely removed from the cartridge 60; subsequently the rotary actuator 67 turns the cartridge 60 by one chamber angle so that the next chamber 62 with the test-element 16 is in line with the shifter 70. As soon as a measurement request is signalized by the customer, the shifter 70 moves the test-element 16 from the chamber 62 into the measuring position so that the measurement can start.

Figure 5:
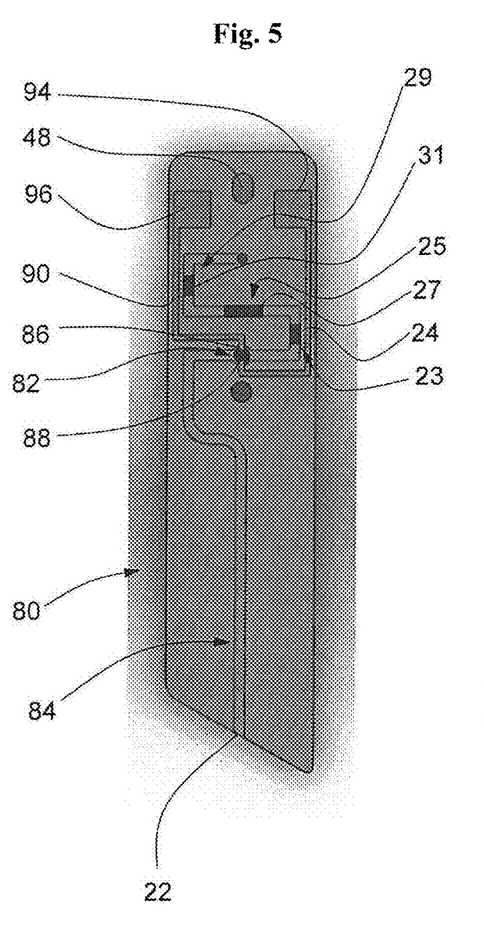
FIG. 5 shows an embodiment of an electrochemical-optical test-element in a front view.
Figure 6:
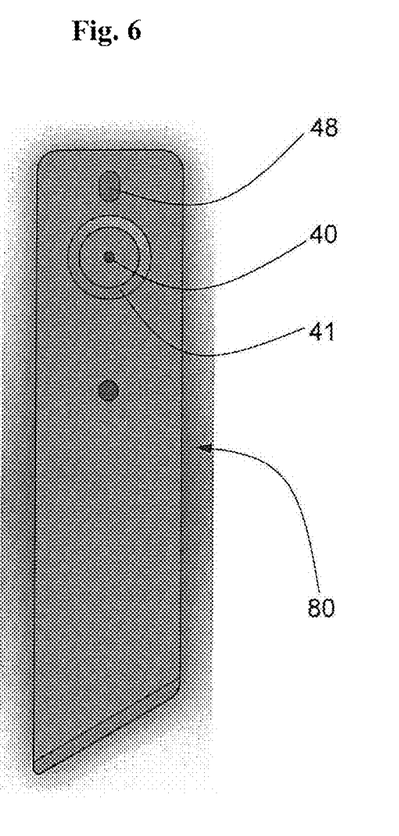
FIG. 6 shows a rear view of the test-element of FIG. 5.

FIG. 5 and FIG. 6 show the front view and the rear view of embodiments of a test-element 80. The test-element 80 is an electrochemical-optical test-element which is provided with an electrochemical-optical measuring section 82 in the sample-line 84. The measuring section 82 is provided with two electrodes 86, 88 positioned opposite to each other, the electrodes being connected through electric lines 90, 92 with contacts 94, 96. The contacts 94, 96 are arranged in line to respective contacts of the basic unit whereby the contacts are connected with the electrochemical analyzer of the basic unit. The measuring section 82 is furthermore provided with an optical measuring track for the photometer.

Behind the measuring section 82, as seen from the inlet opening 22, is a first reagent section 23 with a first reagent 24 which is a key-reagent 24. Behind the first reagent section 23 is a second reagent section 25 with a second reagent 27 which is a first auxiliary-agent 27. Adjacent to the second reagent section 25 is a third reagent section 29 with a third reagent 31 which is a second auxiliary-agent 31. Both auxiliary-agents 27, 31 are analyte-standards with different quantities or concentrations, respectively.

The backside of the test-element of FIG. 6 is provided with the pump opening 40 as a pump element of the test-element 80. A circular seal element 41 is provided surrounding the pump opening 40 to provide a gas-tight connection between the sample-line 84 and a sample-pump realized as a pump actuator 42.

Figure 7:
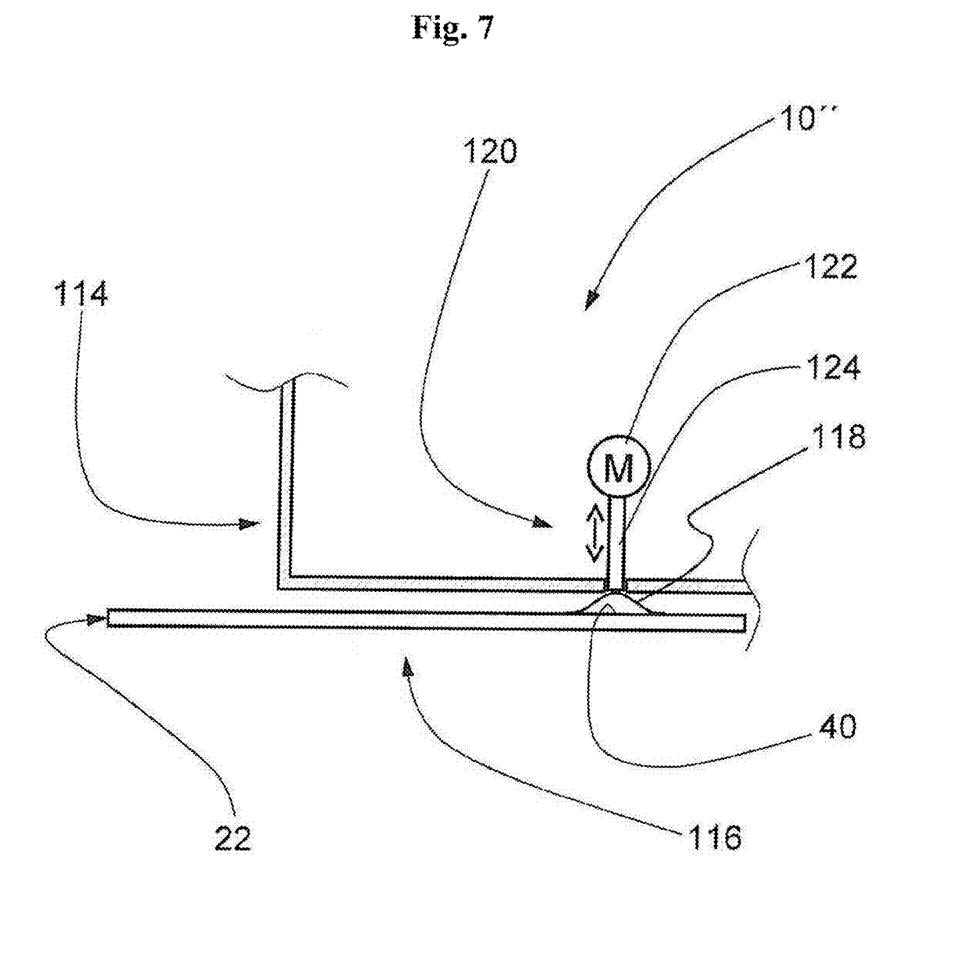
FIG. 7 shows a side view of an embodiment of a test-element with a pump membrane, which is controlled via a pump actuator from the basic unit.

FIG. 7 schematically shows a side view of a part of an embodiment of a mobile water-analyzing system 10". The water-analyzing system 10" is provided with a disposable test-element 116 which is provided with a convex and vesicular pump membrane 118 above the pump opening 40. The pump element, which is formed as a pump membrane, 118 has a pump volume which is higher than the total volume of the sample-line 84.

The basic unit 114 is provided with a pump actuator 120 with a motor 122 whereby the pump actuator 120 controls a rod 124. The rod 124 pushes the pump membrane 118 of the inserted disposable test-element 116. The water-sample can be moved over the complete length of the sample-line forward and backward by the rod 124 deforming the pump membrane 118.

To determine an analyte in a water-sample, a test-element 16 is first inserted into the test-element receptacle of the basic unit 14. The basic unit 14 can, for example, be activated thereby. In a next step, the inlet opening 22 of the test-element is immersed manually into the analyzing water-reservoir 12 so that the sample-pump 42 sucks a water-sample into the measuring section 28 of the sample-line 20. The analyzer 30 determines in a first analysis the background signal of the water-sample in the measuring section.

As soon as the background signal determination is finished, the water-sample is pumped forward from the measuring section 28 into the first reagent section 23. The water-sample meets the key-reagent as the first reagent 24 in the first reagent section 23 so that the key-reagent is mixed with the water-sample. The key-reagent reacts with the analyte in the water-sample so that the optical properties of the water-sample change.

By pumping backwards, the water-sample flows back from the first reagent section 23 to the measuring section 28. The water-sample is analyzed a second time photometrically by the analyzer 30. The result of the second measurement is a gross-value. Subtracting the background from the gross-value leads to a net concentration of the analyte in the water-sample.

With the test-element 80 of FIG. 5 and FIG. 6, an even more precise determination of the analyte in a water-sample can be realized by using standard addition. After the determination of the analyte in the measuring section 82, the water-sample is again pumped forward to the second reagent section 23 which is provided with a second reagent 27. The second reagent 27 is a first auxiliary-agent which is an analyte-standard. The water-sample is mixed with the second reagent 27 in the second reagent section 25. The water-sample is then pumped backwards from the second reagent section 25 into the measuring section 82, whereby the water-sample is analyzed a third time photometrically. The water-sample is again transported forward to the third reagent section 29, whereby the water-sample is mixed with the third reagent 31 which defines a second analyte standard and which is a second auxiliary-reagent. Finally, the water-sample is again transported backwards from the third reagent section 29 to the measuring section 82, whereby the water-sample is measured a fourth time by the photometer.

Both photometrical analyte standard measurements lead to a concentration-absorption characteristic line which allows an exact determination of the analyte concentration of the water-sample by using the net concentration value.

Reagents 24, 27, 31 can alternatively be auxiliary-reagents of another kind.

The auxiliary-reagent can also be a neutralization-reagent. After the water-sample has been analyzed in the measuring section 28, the water-sample is pumped to the auxiliary-reagent which reacts with the key-reagent in such a manner that the key-reagent is neutralized so that the test-element can be disposed of, for example, in the household trash.

The auxiliary-reagent can also gelatinize and/or color the water-sample after the water-sample has been analyzed. A change of the color of the water-sample shows the customer that the test-element has been used. The change of the color can also be detected by the analyzer. Gelatinizing causes a fixation of the water-sample in the sample-line so that leakage is avoided.

The auxiliary-reagent can also be an activator which activates the key-reagent. The auxiliary-agent and the key-reagent must be arranged in line. The auxiliary-reagent activates the key-reagent as soon as key-reagent is being mixed with the auxiliary-reagent in the water-sample. The key-reagent as well as the auxiliary-reagent can be positioned between measuring section 28 and pump opening 40 or alternatively between inlet opening 22 and measuring section 28.

The present invention is not limited to embodiments described herein; reference should be had to the appended claims.

The invention claimed is:

1. A method for determining an analyte in a water sample with a mobile water analysis system having a basic unit and a test element insertable in the basic unit, the method comprising:
  providing the test element comprising:
    a microfluidic sample line comprising:
      an inlet opening disposed at a first end, the inlet opening being configured to receive the water sample,
      a pump port disposed at a second end of the microfluidic sample line,
      an inlet section disposed between the inlet opening and the pump port,
      a measuring section comprising at least one window arranged at an end of the measuring section, the measuring section being arranged between the inlet section and the pump port and being coincident with a sample pathway,
      a first reagent section disposed between the measuring section and the pump port, and
      a reagent disposed in the first reagent section of the microfluidic sample line;
  providing the basic unit comprising:
    a photometer comprising a light source configured to generate a measurement beam and a light detector configured to receive the measurement beam,
    a test element receptacle configured so as to allow the test element to be inserted into the test element receptacle,
    a photometric measuring track, the photometric measuring track being defined by the measuring section when the test element is inserted into the element receptacle, the measurement beam and the photometric measuring track being aligned during a photometric measurement so that the photometric measurement occurs along a length of each of the photometric measuring track and the measuring section, and not in a cross direction thereto, and
    a pump actuator cooperatively connected with the pump opening port, the pump actuator being configured to pump the water sample into, and back and forth through, the microfluidic sample line;
  inserting the test element into the test element receptacle of the basic unit;
  transporting the water sample from the inlet opening to the measuring section by activating the pump actuator;
  performing a first analysis of the water sample in the measuring section with the photometer to determine a background signal of the water sample;

transporting the water sample from the measuring section to the first reagent section by activating the pump actuator, wherein the water sample mixes with the reagent;

transporting the water sample from the first reagent section to the measuring section by activating the pump actuator; and performing a second analysis of the water sample in the measuring section with the photometer to determine a gross value of the water sample.

2. The method as recited in claim 1, wherein the microfluidic sample line further comprises a second reagent section with a second reagent disposed between the first reagent section and the pump port, and wherein, after performing the second analysis, the method further comprises:

transporting the water sample to the second reagent section by activating the pump actuator, wherein the water sample mixes with the second reagent.

3. The method as recited in claim 2, wherein, after transporting the analyzed water sample to the second reagent section, the method further comprises:

transporting the water-sample from the second reagent section to the measuring section by activating the pump actuator; and performing a third analysis of the water sample with the photometer.

4. The method as recited in claim 3, wherein the microfluidic sample line further comprises a third reagent section with a third reagent disposed between the second reagent section and the pump port, and wherein, after performing the third analysis of the water sample, the method further comprises:

transporting the water sample to the third reagent section by activating the pump actuator, wherein the water sample mixes with the third reagent;

transporting the water sample from the third reagent section to the measuring section by activating the pump actuator; and performing a fourth analysis of the water sample in the measuring section with the photometer.

5. A mobile water analysis system for performing the method as recited in claim 1, the mobile water analysis system comprising a basic unit and a test-element insertable in the basic unit, wherein, the test element comprises:
a microfluidic sample line comprising:
an inlet opening disposed at a first end, the inlet opening being configured to receive the water sample,
a pump port disposed at a second end of the microfluidic sample line,
an inlet section disposed between the inlet opening and the pump port,
a measuring section comprising at least one window arranged at an end of the measuring section, the measuring section being arranged between the inlet section and the pump port and being coincident with a sample pathway,
a first reagent section disposed between the measuring section and the pump port, and
a reagent disposed in the first reagent section of the microfluidic sample line; and the basic unit comprises:
a photometer comprising a light source configured to generate a measurement beam and a light detector configured to receive the measurement beam,
a test element receptacle configured so as to allow the test element to be inserted into the test element receptacle,
a photometric measuring track, the photometric measuring track being defined by the measuring section when the test element is inserted into the test element receptacle, the measurement beam and the photometric measuring track being aligned during a photometric measurement so that the photometric measurement occurs along a length of each of the photometric measuring track and the measuring section, and not in a cross direction thereto, and
a pump actuator cooperatively connected with the pump port.

6. The mobile water analysis system as recited in claim 5, wherein the basic unit and the test element each further comprise at least one contact and the measuring section includes at least one electrode, wherein the at least one electrode is connected with the photometer through the at least one contact of the basic unit and the test element.

7. The mobile water analysis system as recited in claim 5, wherein the photometer is a transmission photometer.

8. The mobile water analysis system as recited in claim 5, wherein the test element further comprises a pump membrane, and the pump actuator of the basic unit is configured to control the pump membrane.

9. The mobile water analysis system as recited in claim 1, wherein the test element is prefabricated.

10. The mobile water analysis system as recited in claim 1, wherein the test element is prefabricated.

11. The method as recited in claim 1, further comprising:
subtracting the background signal of the water sample from the gross value of the water signal so as to obtain a net concentration of the analyte in the water sample.

12. The method as recited in claim 2, wherein the second reagent is at least one of second auxiliary-reagent, a neutralization-reagent configured to neutralize the reagent, a gelatinizing reagent configured to gelatinize the reagent, and a coloring reagent configured to color the reagent.

13. The method as recited in claim 3, further comprising:
determining a concentration-absorption characteristic line; and
determining an exact analyte concentration of the water sample.

14. The method as recited in claim 4, wherein the third reagent is at least one of second auxiliary-reagent, a neutralization-reagent configured to neutralize the reagent, a gelatinizing reagent configured to gelatinize the reagent, and a coloring reagent configured to color the reagent.

15. The method as recited in claim 4, further comprising:
determining a concentration-absorption characteristic line; and
determining an exact analyte concentration of the water sample.

16. A mobile water analysis system as recited in claim 5, wherein the microfluidic sample line of the test element further comprises:
a second reagent section disposed between the first reagent section and the pump port; and
a second reagent disposed in the second reagent section.

17. A mobile water analysis system as recited in claim 16, wherein the microfluidic sample line of the test element further comprises:
a third reagent section disposed between the second reagent section and the pump port; and
a third reagent disposed in the third reagent section.

* * * * *